US012508368B1

(12) United States Patent
Dragan

(10) Patent No.: US 12,508,368 B1
(45) Date of Patent: Dec. 30, 2025

(54) DENTAL ANESTHETIC BUFFERING SYSTEM

(71) Applicant: Centrix, Inc., Shelton, CT (US)

(72) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 749 days.

(21) Appl. No.: 17/881,476

(22) Filed: Aug. 4, 2022

Related U.S. Application Data

(60) Provisional application No. 63/231,335, filed on Aug. 10, 2021.

(51) Int. Cl.

| | |
|---|---|
| ***A61M 5/24*** | (2006.01) |
| ***A61J 1/14*** | (2023.01) |
| ***A61J 1/20*** | (2006.01) |

(52) U.S. Cl.
CPC .......... *A61M 5/2448* (2013.01); *A61J 1/1406* (2013.01); *A61J 1/2096* (2013.01); *A61M 5/2459* (2013.01); *A61M 2202/048* (2013.01)

(58) Field of Classification Search
CPC .. A61M 5/2448; A61M 5/284; A61M 5/2066; A61M 15/0063; A61M 2209/06; A61J 1/00; A61J 1/2096; B65B 3/00; B65B 35/00; B65B 35/02; B65D 5/00; A61B 50/30
See application file for complete search history.

(56) References Cited

U.S. PATENT DOCUMENTS

| | | | | |
|---|---|---|---|---|
| 3,796,218 A * | 3/1974 | Burke | A61M 5/31596 604/411 |
| 4,328,802 A * | 5/1982 | Curley | A61J 1/2096 604/88 |
| 5,261,903 A | 11/1993 | Dhaliwal et al. | 604/416 |
| 5,603,695 A | 2/1997 | Erickson | 604/89 |
| 5,795,330 A | 8/1998 | Tofighi et al. | 604/82 |
| 6,474,375 B2 | 11/2002 | Spero et al. | 141/329 |
| 6,746,438 B1 | 6/2004 | Arnissolle | 604/411 |
| 6,817,987 B2 | 11/2004 | Vetter et al. | 604/85 |
| 6,948,522 B2 | 9/2005 | Newbrough et al. | 137/550 |
| 7,077,835 B2 | 7/2006 | Robinson et al. | 604/413 |

(Continued)

OTHER PUBLICATIONS

Solvay, "Sodium Bicarbonate (S300) Batch Numbering and Shelf Life Statement", 2018 (Year: 2018).*

(Continued)

*Primary Examiner* — Kevin C Sirmons
*Assistant Examiner* — Antarius S Daniel
(74) *Attorney, Agent, or Firm* — Fattibene and Fattibene, LLC; Paul A. Fattibene

(57) ABSTRACT

A dental anesthetic buffering system using pre-dosed dry buffering material. Liquid dental anesthetic from a standard anesthetic cartridge or carpule is injected into a dry buffering material buffering the anesthetic improving efficacy and comfort. A buffer dosing cartridge or carpule configured to fit within an anesthetic syringe is pre-dosed with a dry buffering material and injected with a liquid anesthetic from a standard anesthetic cartridge or carpule forming a buffered anesthetic cartridge or carpule. The buffered anesthetic cartridge or carpule is placed in an anesthetic syringe used to immediately administer the buffered anesthetic to a patient. Ease-of-use, effectiveness, and comfort to the patient are provided making dentistry easier.

3 Claims, 3 Drawing Sheets

(56) References Cited

U.S. PATENT DOCUMENTS

| | | | | |
|---|---|---|---|---|
| 7,462,164 | B2 | 12/2008 | Moir | 604/82 |
| 7,695,449 | B2 | 4/2010 | Wang et al. | 604/82 |
| 7,736,353 | B2 | 6/2010 | Reynolds | 604/414 |
| 8,162,917 | B2 | 4/2012 | Stepovich et al. | 604/415 |
| 8,303,566 | B2 | 11/2012 | Stepovich et al. | 604/413 |
| 8,317,743 | B2 | 11/2012 | Denenburg | 604/82 |
| 8,672,878 | B2 | 3/2014 | Finke | 604/87 |
| 8,690,853 | B2 | 4/2014 | Stepovich et al. | 604/413 |
| 9,265,697 | B2 | 2/2016 | Stepovich et al. | A61J 1/14 |
| 9,265,894 | B2 | 2/2016 | Finke | A61M 5/31596 |
| 9,616,176 | B2 | 4/2017 | Just | A61M 5/2459 |
| 10,010,482 | B2 | 7/2018 | Davidian et al. | A61J 1/2096 |
| 10,307,336 | B1 | 6/2019 | Sands | A61J 1/201 |
| 10,493,206 | B1 | 12/2019 | Sadek | A61M 5/284 |
| 10,632,261 | B2 | 4/2020 | Pounds et al. | A61M 5/2448 |
| 2010/0298768 | A1* | 11/2010 | Halili, Jr. | A61M 5/24<br>604/87 |
| 2011/0166543 | A1* | 7/2011 | Stepovich | A61J 1/1406<br>604/413 |
| 2014/0312109 | A1* | 10/2014 | Weston | B65D 5/6655<br>229/120.08 |
| 2019/0184103 | A1 | 6/2019 | Johnson et al. | A61M 5/2425 |
| 2020/0046609 | A1 | 2/2020 | Kaedle | A61J 1/2093 |
| 2020/0375847 | A1* | 12/2020 | Frame | A61J 1/2013 |

OTHER PUBLICATIONS

Brian E. Sayre, Terrence Prettyman, and Gagan Kaushal, "Extended Stability of Sodium Bicarbonate Infusions Prepared in Polyolefin Bags", Jul. 2012, Thomas Land Publishers, 538 (Year: 2012).*

Daniel Davidian , "Using Buffered Anesthesia and injection Techniques", Mar. 2017, CDE World (Year: 2017).*

* cited by examiner

DENTAL ANESTHETIC BUFFERING SYSTEM

RELATED APPLICATION

This application claims the benefit of U.S. Provisional Application No. 63/231,335 filed Aug. 10, 2021, which is herein incorporated by reference.

FIELD OF THE INVENTION

The present invention relates in general to dental anesthetics, and particularly to a system for buffering the dental anesthetic just prior to use.

BACKGROUND OF THE INVENTION

Dental anesthetics are used in many dental applications. However, dental anesthetics are acidic in nature that results in discomfort to the patient. The acidic nature of the dental anesthetic improves shelf life and stability. A buffer solution, such as a solution of sodium bicarbonate, is often used to alkalinize the dental anesthetic prior to use. However, the buffer solution cannot be added well prior to the dental anesthetics use. If the buffer solution is added to the dental anesthetic to long prior to use, the shelf life, stability, and efficacy of the dental anesthetic will be significantly reduced. Therefore the dental anesthetic must be buffered just prior to use so as to improve comfort and efficacy of the dental anesthetic for the patient.

The standard dental anesthetic syringe receives a standard dental anesthetic cartridge or carpule containing the acidic dental anesthetic. The dental anesthetic is acidic so as to provide a stable and long shelf life. The standard dental anesthetic cartridge or carpule generally comprises and is defined herein as a plastic or glass tube containing the dental anesthetic having a cap on one end with a pierceable membrane and a fee piston placed in an opposing open end of the tube. When the standard dental anesthetic cartridge or carpule is placed in the dental anesthetic syringe, the membrane of the standard cartridge or carpule is pierced by a hollow needle and the piston is advanced by a plunger of the dental anesthetic syringe forcing the dental anesthetic through the hollow needle for delivery to a patient.

Many devices and processes have been developed in an effort to add a buffer solution to a dental anesthetic. However, many of these devices and processes are complex, costly, and difficult to use and are not easily made applicable to a standard dental anesthetic syringe. Many of the existing devices for using buffer solutions with dental anesthetic require specialized equipment and supplies and training.

One such device is used for filling syringes for dental anesthetic applications is disclosed in U.S. Pat. No. 10,010,482 issuing to Davidian et al. on Jul. 3, 2018 and entitled "Syringe Fill System and Method", herein incorporated by reference. Therein disclosed is a device for filling a syringe at the point of use from a first fluid supply assembly and a second supply assembly. A selector/driver assembly is coupled to rotary knob 26 and a detent knob 28 to dial a selected dose. Anesthetic and buffering medium may be supplied to a syringe filling manifold from separate anesthetic and buffer medium supply containers.

Another device used to buffer an anesthetic is disclosed in United States Patent Application Publication No. 2020/0375847 issuing to Frame et al. on a Dec. 3, 2020 and entitled "Anesthetics Needle Device to Facilitate the use of Buffered Anesthetics", herein incorporated by reference.

Therein disclosed is a buffer cartridge for storing and moving a buffer solution into a syringe having an anesthetic carpule. A relatively complex anesthetic needle device is used. The anesthetic needle device requires an exhaust needle and a transfer needle to transfer a buffered solution into an anesthetic cartridge or carpule and remove a portion of the anesthetic.

While prior devices and processes have worked adequately they are generally complex, costly to manufacture, and expensive. Therefore there is a need to provide a simpler and cost-effective solution to buffer a dental anesthetic making dentistry easier.

SUMMARY OF THE INVENTION

The present invention is a simple and cost-effective system for easily and quickly buffering a dental anesthetic immediately prior to use. A vial containing a dry buffering material, such as dry powdered sodium bicarbonate, has a pierceable membrane seal covering an open end. The dry buffering material contained in the vial is very stable and has a long shelf life.

In one embodiment, a standard dental anesthetic cartridge or carpule contains a stable acidic liquid anesthetic. The liquid anesthetic is injected with a standard anesthetic syringe into the vial. After the acidic anesthetic is mixed with the dry buffering material, the buffered anesthetic is drawn back into the standard dental anesthetic cartridge or carpule. The buffered anesthetic is then ready to immediately be used on a patient. Preferably, a plurality of vials containing different preselected doses of a dry buffering material is provided permitting the dentist to select an appropriate dose of dry buffering material for buffering the anesthetic suitably for the application and patient.

In another embodiment a standard anesthetic cartridge or carpule, that can be directly placed within a standard anesthetic syringe, is prepared with only a dry buffering material contained therein. The standard anesthetic cartridge or carpule containing the dry buffering material is injected with the acidic anesthetic and mixed. The standard anesthetic cartridge or carpule containing the buffered anesthetic is now directly placed in a standard anesthetic syringe for immediate use in a standard anesthetic syringe. Preferably, a plurality of standard anesthetic cartridges or carpules is provided permitting the selection of an appropriate dose for buffering the anesthetic suitably for the application and patient.

Accordingly it is an object of the present invention to simplify and make easier the buffering of a dental anesthetic immediately prior to use.

It is another object of the present invention to provide improved comfort to a patient during an injection of dental anesthetic.

It is an advantage of the present invention that the buffering material is stable for prolonged storage or shelf live.

It is another advantage of the present invention that standard anesthetic syringes and standard anesthetic cartridges or carpules may be used.

It is a feature of the present invention that a dry buffering material is used.

It is another feature of the present invention that a plurality of vial or standard anesthetic cartridges or carpules is provided with each containing a different dose of the dry buffering material.

These and other objects, advantages, and features will become readily apparent in view of the following detailed description.

DETAILED DESCRIPTION OF THE PREFERRED EMBODIMENTS

Figure 1:
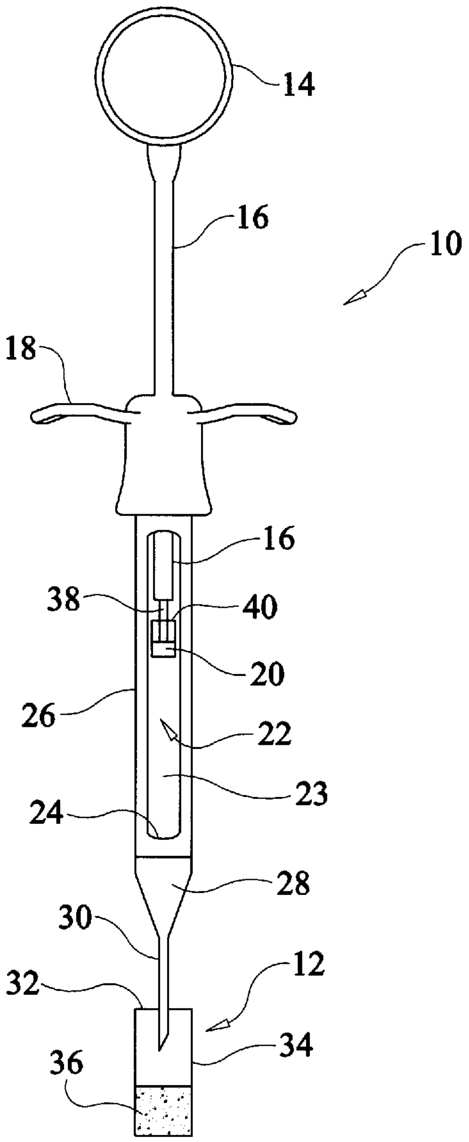
FIG. 1 schematically illustrates the present invention comprising a standard dental anesthetic syringe containing a standard anesthetic cartridge or carpule and a vial containing a dry buffering material.

FIG. 1 schematically illustrates an embodiment of the present invention. A standard dental anesthetic syringe 10 has a thumb ring 14 attached to a plunger 16 passing through a finger flange 18 into a barrel 26 with the breach opening 24. A standard dental anesthetic syringe 10 is herein defined as syringe capable of receiving a standard dental anesthetic cartridge or carpule. Attached to the end of the standard dental anesthetic syringe 10 is a needle hub 28 having a double ended hollow needle with a lower hollow or hypodermic needle 30. Placed within the breach opening 24 is a standard anesthetic cartridge or carpule 22 comprising a plastic or glass tube 23 containing a liquid dental anesthetic that is acidic to improve stability and prolong shelf life. The tube 23 has a top open end 40 with a free piston 20 placed therein. A piston spear 38 is placed on the distal end of the plunger 16. The piston spear 38 attaches to the piston 20 so that the speared piston 20 is capable of being moved up-and-down within the tube 23 when the thumb ring 14 moves the plunger 16 up-and-down within the barrel 26 of the anesthetic syringe 10. Accordingly, movement of the thumb ring 14 and plunger 16 with the piston 20 attached to the piston spear 38 permits a dental liquid anesthetic contained within the tube 23 to be expressed from or drawn into the tube 23. While no other external mechanisms are illustrated, it should be appreciated that a mechanism could be attached to the finger flange 18 or barrel 26 of the anesthetic syringe 10 and the thumb ring 14 to assist or automate movement of the plunger 16 and the attached piston 20 to aid in expressing or drawing the liquid anesthetic from or into the tube 23 of the standard anesthetic cartridge or carpule 22. Additionally, the piston spear 38 may be enhances with barbs, corkscrew, or other enhanced shapes to securely engage the piston 20 so as to hold the piston 20 during moving the piston 20 away from the needle hub 28.

A vial 12 comprises a container 34 containing a dry buffering material 36, preferably dry powder sodium bicarbonate, having a pierceable membrane top 32. The membrane top 32 is pierced by the lower hollow or hypodermic needle 30 of the standard anesthetic syringe 10. The dry buffering material 36 provides an effective dose to buffer or reduce the acidity of the acidic anesthetic contained in the anesthetic cartridge or carpule 22. The use of a dry buffering material 36, contained within the vial 12, results in the buffering material 36 to be very stable with a long shelf life. Additionally, this permits the vials 12 to be safely and easily shipped at low cost due to their low weight.

In operation or in practicing the present invention a standard anesthetic cartridge or carpule 22 is placed within the standard anesthetic syringe 10 and the lower hollow or hypodermic needle 30 pierces the membrane 32 of the vial 12 containing the dry buffer material 36. The acidic liquid anesthetic contained within the standard anesthetic cartridge or carpule 22 is expressed into the vial 12 and mixed with the dry buffer material 36. As a result the buffer material 36 lowers the acidity and alkalizes or increases the pH of the acidic anesthetic to be more neutral resulting in a buffered anesthetic. The buffered anesthetic is drawn into the standard anesthetic cartridge or carpule 22 by moving the thumb ring 14 and plunger 16 upward away from the lower hollow or hypodermic needle 30 moving the piston 20 towards the finger flange 18. Accordingly, the buffered anesthetic is drawn from the vial 12 into the standard anesthetic cartridge or carpule 22 ready to immediately be used for a patient.

Figure 2:
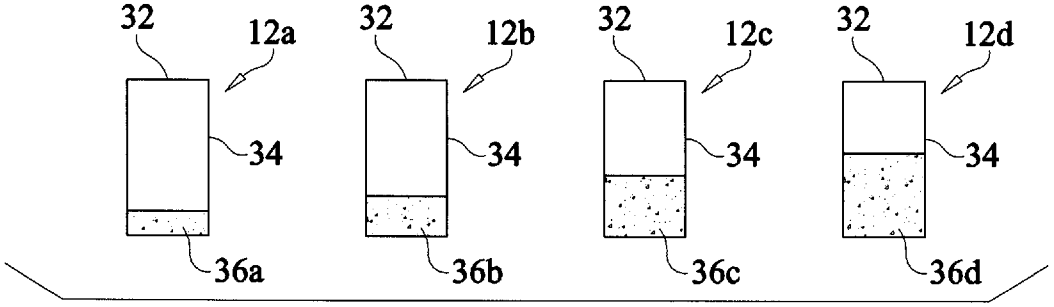
FIG. 2 schematically illustrates the present invention comprising a plurality of vials containing different amounts or doses of a dry buffering material.

FIG. 2 schematically illustrates an embodiment of the present invention using a plurality of vials containing different doses of a buffering material. In FIG. 2 four different vials 12*a*, 12*b*, 12*c*, and 12*d* are illustrated, with each vial 12*a*, 12*b*, 12*c* and 12*d* comprising a container 34 having a pierceable membrane 32. Each of the vials 12*a*, 12*b*, 12*c* and 12*d*, contain a different quantity or dose of a dry buffering material 36*a*, 36*b*, 36*c*, and 36*d*. The range of dry buffering materials 36*a*, 36*b*, 36*c*, and 36*d* may range from a lowest dose of buffering material 36*a* to a highest dose of buffering material 36*d*. The dose range of the buffering materials 36*a*, 36*b*, 36*c*, and 36*d* should be within a range in which a dentist is expected to use in deciding on treatment of a patient. The dentist can select the predetermined dose from within the range of doses suitable for a specific patient and dose of anesthetic.

Figure 3:
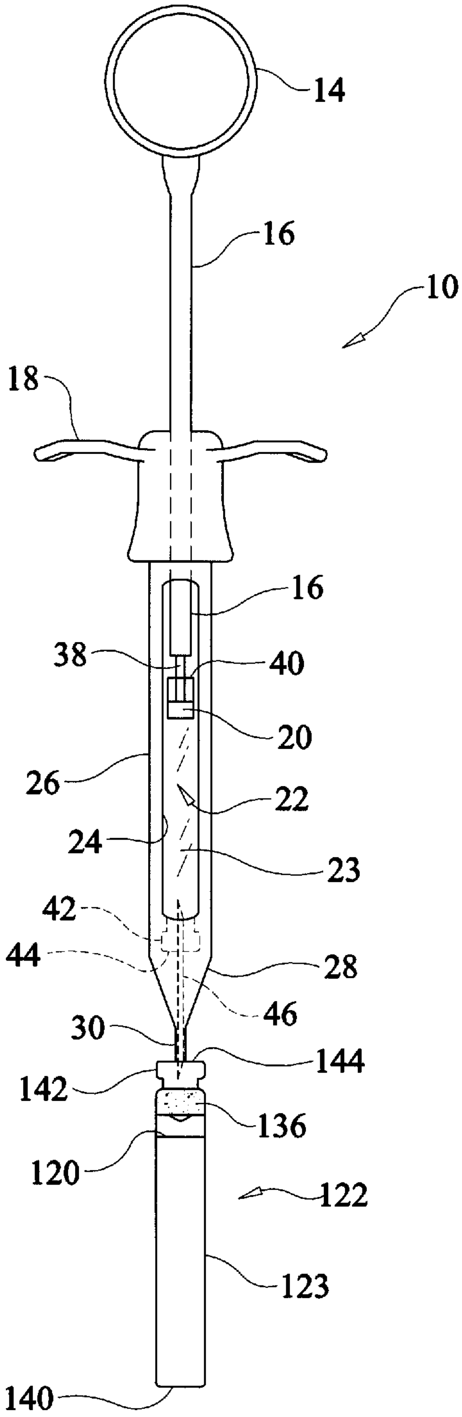
FIG. 3 schematically illustrates another embodiment of the present invention comprising a standard dental anesthetic syringe containing a standard anesthetic cartridge or carpule and a standard anesthetic cartridge or carpule containing only a dry buffering material.
Figure 4:
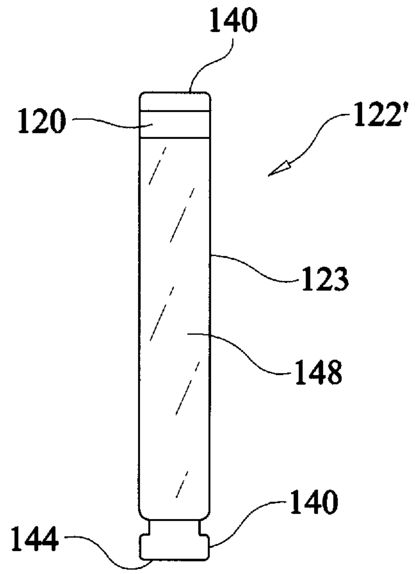
FIG. 4 schematically illustrates a standard dental anesthetic cartridge or carpule containing a buffered liquid anesthetic.

FIGS. 3 and 4 schematically illustrate another embodiment of the present invention. In this embodiment a standard dental anesthetic cartridge or carpule is used for containing the dry buffering material. In FIGS. 3 and 4 the anesthetic syringe 10 holds a standard dental anesthetic cartridge or carpule 22 comprising a membrane cap 42 having a pierceable membrane 44 and an opposing top open end 40 containing a piston 20 containing a liquid anesthetic. The needle hub 28 has an upper hollow or hypodermic needle 46 and a lower hollow or hypodermic needle 30.

A buffer dosing cartridge or carpule 122 contains a buffering dose 136 of dry or powdered buffering material, preferably sodium bicarbonate. The buffer dosing cartridge or carpule 122 has the same structure as a standard dental anesthetic cartridge or carpule, but without the liquid anesthetic. Therefore the buffer dosing cartridge or carpule 122 is adapted or configured to fit directly within the anesthetic syringe 10. The buffer dosing cartridge or carpule 122 has a membrane cap 142 with a pierceable membrane 144 placed on one end of the tube 123 and a free piston 120 placed in an opposing open end 140 of the tube 123. The piston 120 is advanced upward adjacent or next to the dry or powdered buffering material 136 in the buffer dosing cartridge or carpule 122 so as to leave no room for air.

In FIG. 3 the buffer dosing cartridge or carpule 122 is illustrated having the lower hollow or hypodermic needle 30 passing through pierceable membrane 144. The liquid anesthetic from the standard anesthetic cartridge or carpule 22 within the anesthetic syringe 10 is injected into the buffer dosing cartridge or carpule 122. Upon injecting the liquid anesthetic from the standard anesthetic cartridge or carpule 22 into the buffer dosing cartridge or carpule 122, the free piston is forced away from the membrane cap 142 and the liquid anesthetic mixes with the dry or powdered buffering material 136.

FIG. 4 schematically illustrates a buffered anesthetic cartridge or carpule 122' formed from injecting the buffer dosing cartridge or carpule 122 with the liquid anesthetic from the standard anesthetic cartridge or carpule 22. The buffered anesthetic cartridge or carpule 122' contains the buffered anesthetic 148.

Figure 5:
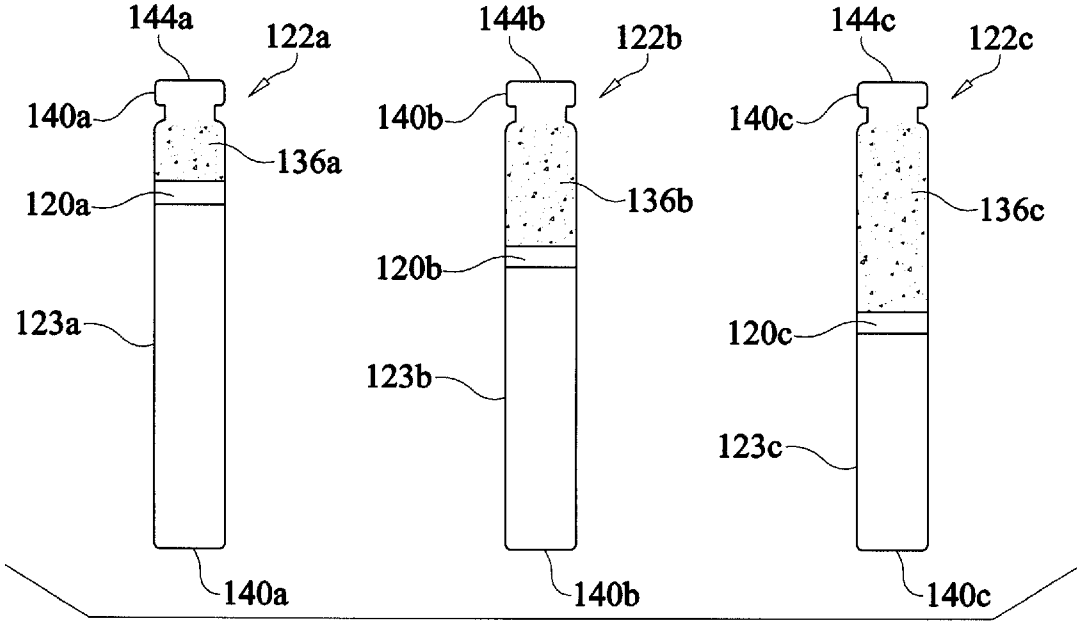
FIG. 5 schematically illustrates the present invention comprising a plurality of standard anesthetic cartridges or carpules containing different doses of only a dry buffering material.

FIG. 5 schematically illustrates an embodiment of the present invention using a plurality of dosing cartridges or carpules 123*a*, 123*b*, and 123*c* containing different doses of a dry or powdered buffering material 136*a*, 136*b*, and 136*c*. In FIG. 5 three different tubes 123*a*, 123*b*, and 123*c* are illustrated, with each tube 123*a*, 123*b*, and 123*c* comprising a membrane cap 140*a*, 140*b*, and 140*c*, each with a respective pierceable membrane 144*a*, 144*b*, and 144*c*. Each of the tubes 123*a*, 123*b*, and 123*c*, contain a different dose of a dry buffering material 136*a*, 136*b*, and 136*c*. The amount or dose of each buffering materials 136*a*, 136*b*, and 136*c* may range from a lowest dose of buffering material 136*a* to a highest dose of buffering material 136*c*. The dose range of the buffering materials 136*a*, 136*b*, and 136*c* should be within a range in which a dentist is expected to use in deciding on treatment of a patient depending upon the anesthetic used. Different anesthetics and anesthetic and epinephrine combinations have different acidity levels and therefore require different buffering doses. The dentist can select the predetermined buffering dose from within the range of buffering doses suitable for a specific patient and anesthetic. Accordingly, the dose of buffering material 136*a* may be a small dose, the dose of buffering material 136*b* may be a medium dose, and the dose of buffering material 136*c* may be a large dose.

In practicing the present invention illustrated in FIGS. 3, 4, and 5 a dentist can easily prepare a buffered anesthetic just prior to application to a patient. A dentist can use a standard dental anesthetic cartridge or carpule 22 placed within the anesthetic syringe 10 to inject a liquid anesthetic into the buffer dosing cartridge or carpule 122 containing the dry or powdered buffer material 136. Upon injecting the anesthetic from the standard dental anesthetic cartridge or carpule 22 the piston 120 in the buffer dosing cartridge or carpule 122 is pushed downward towards the opposing open end 140 of the tube 123. The dry or powdered buffer material 136 is mixed with the liquid anesthetic from the standard dental anesthetic cartridge or carpule 22 to form the desired buffered anesthetic. The resulting buffered anesthetic cartridge or carpule 122' is used to replace the expended standard dental anesthetic cartridge or carpule 22 contained within the anesthetic syringe 10. The dentist then uses the created buffered anesthetic cartridge or carpule 122' placed in the anesthetic syringe 10 for administering the buffered anesthetic to the patient. Depending upon the anesthetic and the patient's needs the dentist can select a predetermined amount or dose of buffering material 136*a*, 136*b*, or 136*c* from the plurality of dosing cartridges or carpules 122*a*, 122*b*, or 122*c* as illustrated in FIG. 5.

The present invention provides a simple and efficient anesthetic buffering system that can be used by the dentist quickly and easily for buffering an anesthetic just prior to use. The use of a dry or powdered buffering material provides a long and stable shelf life reducing waste and uncertainty as to the effectiveness of the buffered anesthetic. The present invention improves comfort for the patient and makes dentistry easier.

Although the preferred embodiments have been illustrated and described, it will be obvious to those skilled in the art that various modifications may be made without departing from the spirit and scope of this invention.

What is claimed is:

1. A method for buffering an acidic liquid dental anesthetic contained within a standard anesthetic cartridge or carpule, the standard anesthetic cartridge or carpule having a membrane cap with a pierceable membrane place on one end and an opposing open end with a piston placed therein comprising the steps of:

placing the standard anesthetic cartridge into an anesthetic syringe;

selecting a dosing cartridge or carpule from one of a plurality of dosing cartridges or carpules, the plurality of dosing cartridges or carpules each having the same structure as the standard anesthetic cartridge or carpule and configured to fit directly within the anesthetic syringe with each one of the dosing cartridges or carpules having a dosing cartridge or carpule piecing membrane and a dosing cartridge or carpule piston, wherein each one of the plurality of dosing cartridges or carpules contains a different dose of a dry buffering material between the dosing cartridge or carpule piecing membrane and the dosing cartridge or carpule piston;

injecting the acidic liquid dental anesthetic contained within the standard anesthetic cartridge or carpule into a selected one of the dosing cartridges or carpules containing a predetermined dose of dry buffering material;

mixing the acidic liquid dental anesthetic with the predetermined dose of dry buffering material in the selected one of the dosing cartridges or carpules forming a buffered anesthetic cartridge or carpule containing a buffered liquid dental anesthetic;

removing the standard anesthetic cartridge from the anesthetic syringe; and placing the buffered anesthetic cartridge or carpule within the anesthetic syringe after said step of removing the standard anesthetic cartridge from the anesthetic syringe wherein the standard anesthetic cartridge is replaced with the buffered anesthetic cartridge, whereby the buffered liquid dental anesthetic is capable of being administered with the anesthetic syringe.

2. The method for buffering an acidic liquid dental anesthetic as in claim 1 wherein:

the dry buffering material comprises sodium bicarbonate.

3. The method for buffering an acidic liquid dental anesthetic as in claim 1 wherein:

the dry buffering material alkalizes the acidic liquid dental anesthetic.

* * * * *